(12) United States Patent
Fujii et al.

(10) Patent No.: US 11,600,182 B2
(45) Date of Patent: Mar. 7, 2023

(54) VEHICLE ALLOCATION SERVICE SYSTEM, VEHICLE ALLOCATION SERVICE METHOD, PROGRAM, AND MOVING OBJECT

(71) Applicant: TOYOTA JIDOSHA KABUSHIKI KAISHA, Toyota (JP)

(72) Inventors: Shinichiro Fujii, Kawasaki (JP); Hiroe Fukui, Toyohashi (JP); Takashi Goto, Okazaki (JP); Tatsuya Shigekiyo, Okazaki (JP); Kuniaki Jinnai, Nagoya (JP); Naoto Sasagawa, Nishio (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 517 days.

(21) Appl. No.: 16/715,591

(22) Filed: Dec. 16, 2019

(65) Prior Publication Data
US 2020/0234595 A1 Jul. 23, 2020

(30) Foreign Application Priority Data
Jan. 18, 2019 (JP) .............................. JP2019-007191

(51) Int. Cl.
*G08G 1/00* (2006.01)
*G05D 1/00* (2006.01)
(Continued)

(52) U.S. Cl.
CPC ........... *G08G 1/202* (2013.01); *A61B 5/0205* (2013.01); *A61B 5/02055* (2013.01);
(Continued)

(58) Field of Classification Search
CPC .. G08G 1/202; A61B 5/0205; A61B 5/02055; A61B 5/1112; A61B 5/1118; A61B 5/14532; A61B 5/14551; A61B 5/369; A61B 5/4869; A61B 5/681; A61B 5/747; A61B 8/08; A61B 5/021; A61B 5/0245;
(Continued)

(56) References Cited

U.S. PATENT DOCUMENTS

| | | | | |
|---|---|---|---|---|
| 5,532,702 A | * | 7/1996 | Mintz | .................... G08G 1/127 342/463 |
| 9,852,599 B1 | * | 12/2017 | Slavin | ...................... A61B 7/04 |

(Continued)

FOREIGN PATENT DOCUMENTS

| | | |
|---|---|---|
| JP | 2002-063690 A | 2/2002 |
| JP | 2003-303239 A | 10/2003 |

(Continued)

*Primary Examiner* — B M M Hannan
(74) *Attorney, Agent, or Firm* — Oblon, McClelland, Maier & Neustadt, L.L.P.

(57) ABSTRACT

A vehicle allocation service system includes an acquisition unit configured to acquire biological information and positional information of a user, a selection unit configured to select a moving object to be provided to the user based on the biological information, a decision unit configured to acquire priority added to a satisfied condition of the biological information of the user and decide an order of vehicle allocation for the selected moving object according to the priority, and an instruction unit configured to instruct the selected moving object to move according to the positional information.

14 Claims, 14 Drawing Sheets

(51) Int. Cl.
*A61B 5/0205* (2006.01)
*A61B 5/00* (2006.01)
*A61B 5/11* (2006.01)
*A61B 8/08* (2006.01)
*A61B 5/1455* (2006.01)
*A61B 5/145* (2006.01)
*A61B 5/369* (2021.01)
*A61B 5/08* (2006.01)
*A61B 5/0245* (2006.01)
*A61B 5/021* (2006.01)
*A61B 8/00* (2006.01)

(52) U.S. Cl.
CPC ........... *A61B 5/1112* (2013.01); *A61B 5/1118* (2013.01); *A61B 5/14532* (2013.01); *A61B 5/14551* (2013.01); *A61B 5/369* (2021.01); *A61B 5/4869* (2013.01); *A61B 5/681* (2013.01); *A61B 5/747* (2013.01); *A61B 8/08* (2013.01); *G05D 1/0011* (2013.01); *G05D 1/0088* (2013.01); *A61B 5/021* (2013.01); *A61B 5/0245* (2013.01); *A61B 5/0816* (2013.01); *A61B 8/4227* (2013.01); *A61B 2562/0219* (2013.01); *G05D 2201/0206* (2013.01)

(58) Field of Classification Search
CPC ............... A61B 5/0816; A61B 8/4227; A61B 2562/0219; A61B 5/318; A61B 5/6893; A61B 5/01; A61B 8/4416; A61B 8/5223; A61B 8/56; A61B 5/18; G05D 1/0011; G05D 1/0088; G05D 2201/0206; G06Q 10/02; G06Q 10/0631; G06Q 30/0645; G06Q 50/30; G06Q 50/10; G06F 16/9535; G06F 16/9537; G16H 50/30

USPC ........................................................... 701/23
See application file for complete search history.

(56) References Cited

U.S. PATENT DOCUMENTS

| | | | |
|---|---|---|---|
| 10,369,967 B2 * | 8/2019 | Sako | B60R 25/305 |
| 2013/0297549 A1 * | 11/2013 | Yano | G06Q 10/04 706/46 |
| 2017/0219367 A1 * | 8/2017 | Liu | H04H 60/64 |
| 2017/0316533 A1 * | 11/2017 | Goldman-Shenhar | H04L 67/306 |
| 2017/0330044 A1 * | 11/2017 | Telpaz | G05D 1/0088 |
| 2018/0113987 A1 * | 4/2018 | Zhu | G16H 50/20 |
| 2018/0144282 A1 * | 5/2018 | Tomiyama | G06Q 50/30 |
| 2018/0158551 A1 * | 6/2018 | Bradley | H04L 63/0861 |
| 2018/0193223 A1 * | 7/2018 | Gal | A61H 33/0095 |
| 2018/0268109 A1 * | 9/2018 | Ramgir | G16H 80/00 |
| 2019/0019146 A1 * | 1/2019 | Chraibi | G08G 1/202 |
| 2019/0087875 A1 * | 3/2019 | Morioka | G06Q 50/10 |
| 2019/0230215 A1 * | 7/2019 | Zhu | H04W 68/005 |
| 2019/0241202 A1 * | 8/2019 | Thomas | B61L 27/16 |
| 2020/0117195 A1 | 4/2020 | Yasui et al. | |
| 2020/0202474 A1 * | 6/2020 | Asukai | G06Q 10/06315 |
| 2021/0405640 A1 * | 12/2021 | Hwang | G05D 1/0088 |

FOREIGN PATENT DOCUMENTS

| | | | |
|---|---|---|---|
| JP | 6338788 B1 | 6/2018 | |
| KR | 20110133884 A * | 12/2011 | ............ G06Q 50/30 |
| WO | WO 2018/230559 A1 | 12/2018 | |
| WO | WO-2019004467 A1 * | 1/2019 | |
| WO | WO-2022200820 A1 * | 9/2022 | ............ G08G 1/123 |

* cited by examiner

FIG. 3

| DEGREE OF EXPANSION OF BLADDER | KIND OF MOVING OBJECT | DEGREE OF EMERGENCY |
|---|---|---|
| 100 TO 120% | TOILET | NORMAL (ARRIVAL WITHIN 30 MINUTES) |
| 120 TO 150% | TOILET | PRIORITY (ARRIVAL WITHIN 15 MINUTES) |
| EQUAL TO OR GREATER THAN 150% | TOILET | HIGHEST PRIORITY (ARRIVAL WITHIN THREE MINUTES) |

FIG. 4

| RANGE OF HEART RATE | KIND OF MOVING OBJECT |
|---|---|
| 0 TO 60 BEATS PER MINUTE | AMBULANCE WITH PHYSICIAN |
| 60 TO 100 BEATS PER MINUTE | GENERAL VEHICLE |
| EQUAL TO OR HIGHER THAN 100 BEATS PER MINUTE | AMBULANCE |

FIG. 5

| RANGE OF BODY TEMPERATURE | KIND OF MOVING OBJECT |
|---|---|
| EQUAL TO OR LOWER THAN 34°C | AMBULANCE WITH PHYSICIAN, HELICOPTER |
| 34 TO 36°C | AMBULANCE |
| 36 TO 38°C | GENERAL VEHICLE |
| 38 TO 40°C | AMBULANCE |
| EQUAL TO OR HIGHER THAN 40°C | AMBULANCE WITH PHYSICIAN, HELICOPTER |

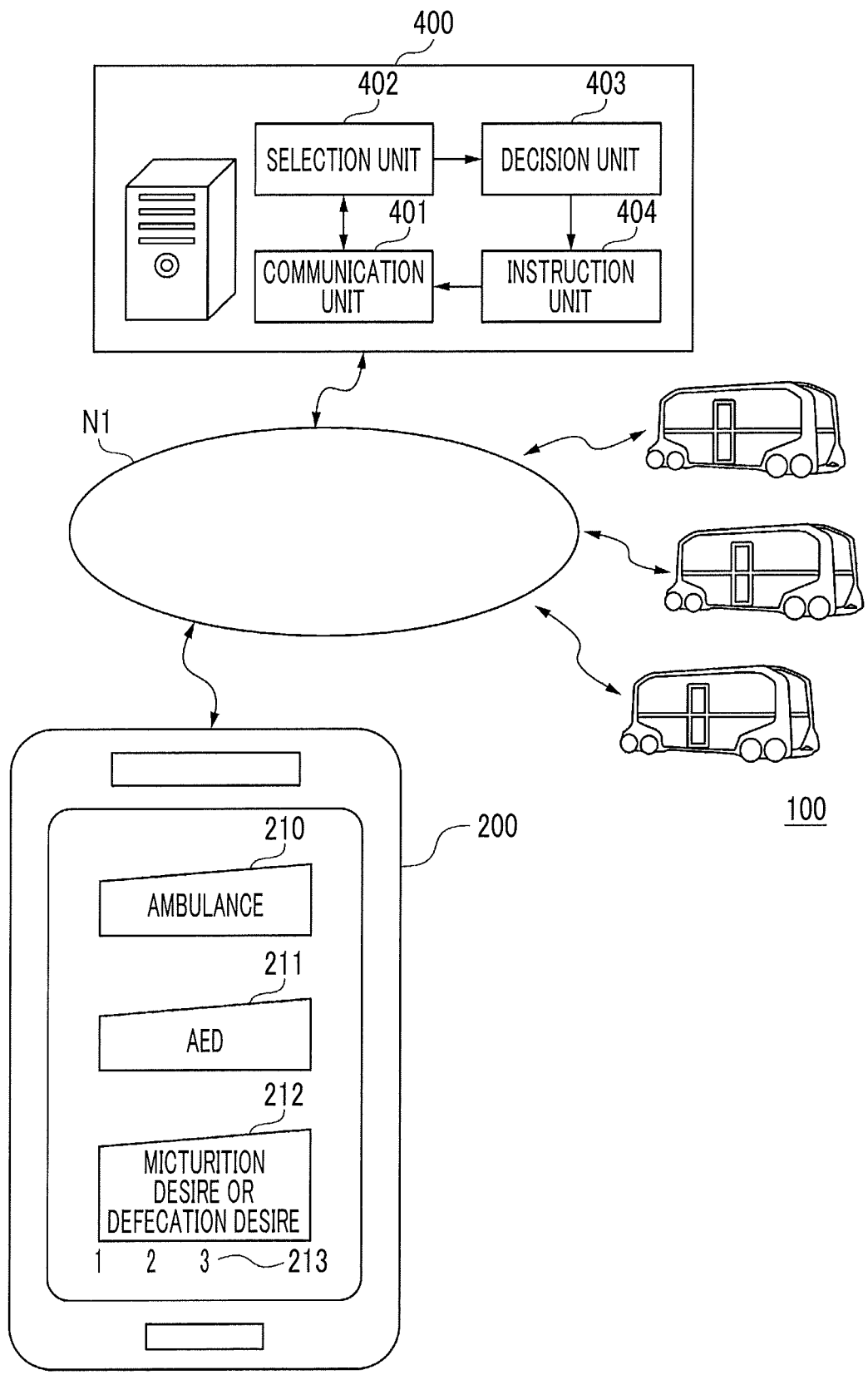

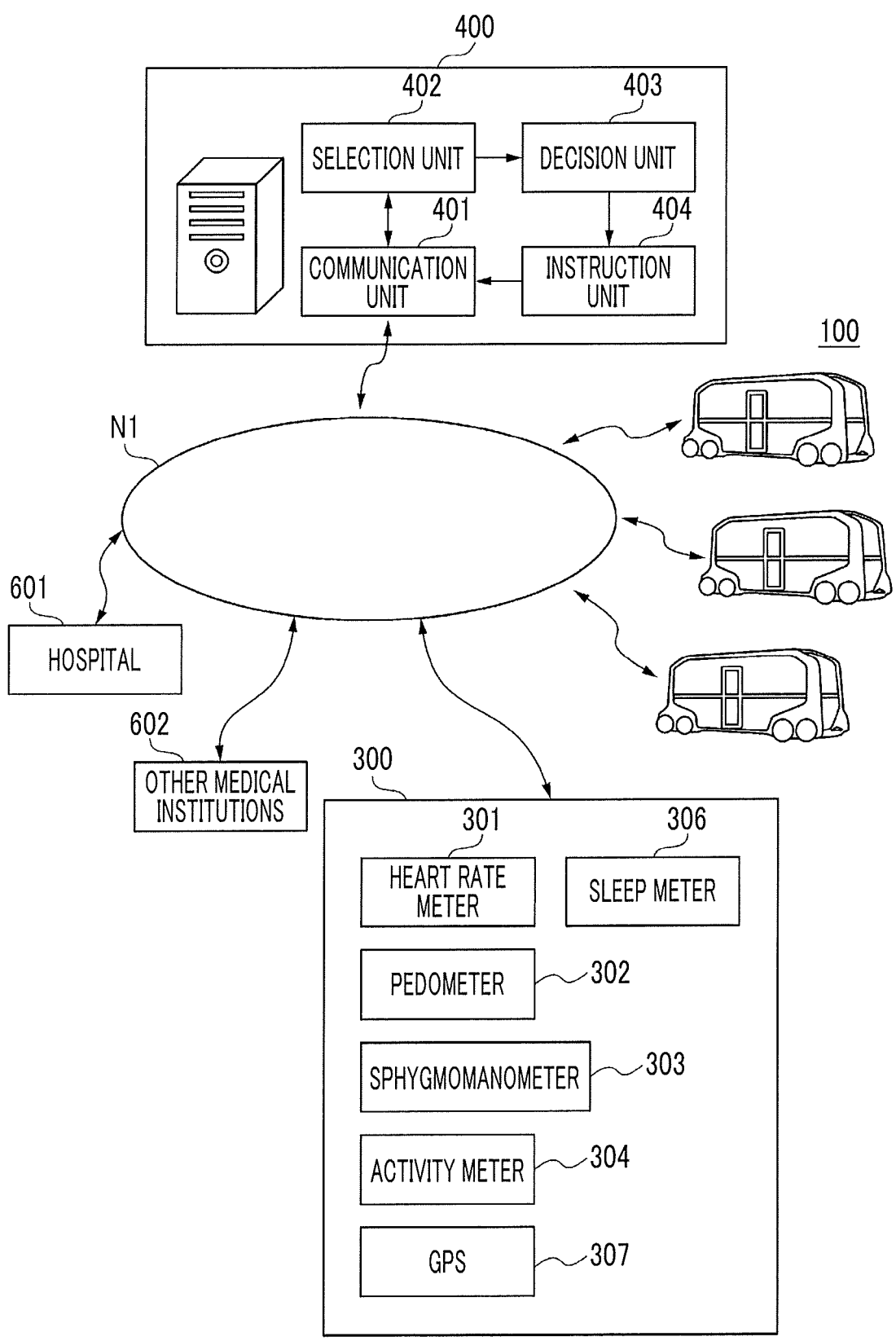

VEHICLE ALLOCATION SERVICE SYSTEM, VEHICLE ALLOCATION SERVICE METHOD, PROGRAM, AND MOVING OBJECT

INCORPORATION BY REFERENCE

The disclosure of Japanese Patent Application No. 2019-007191 filed on Jan. 18, 2019 including the specification, drawings and abstract is incorporated herein by reference in its entirety.

BACKGROUND

1. Technical Field

The present disclosure relates to a vehicle allocation service system, a vehicle allocation service method, a program, and a moving object.

2. Description of Related Art

In the related art, a vehicle allocation service method that allocates a moving object, such as a taxi, according to demand of a user through an online circuit, such as the Internet has been suggested. For example, Japanese Unexamined Patent Application Publication No. 2002-63690 (JP 2002-63690 A) discloses a vehicle allocation service method that can perform optimum vehicle allocation according to demand of a user. In the method, optimum vehicle allocation according to the demand of the user, such as the number of occupants, the vehicle type, or a desired vehicle allocation time, in addition to a desired vehicle allocation position has been suggested. Japanese Patent No. 6338788 (JP 6338788 B) has suggested processing with a plurality of ultrasonic sensors that transmits ultrasonic waves into a body of a subject and detects a bladder, and a server group that estimates a micturition timing based on an expansion rate of the bladder obtained from detection results of the ultrasonic sensors.

SUMMARY

The disclosure has been accomplished in order to solve the problem in the related art, and provides a technique capable of more rapidly executing countermeasures or actions in emergency.

A first aspect of the disclosure relates to a vehicle allocation service system. The vehicle allocation service system includes an acquisition unit, a selection unit, a decision unit, and an instruction unit. The acquisition unit is configured to acquire biological information and positional information of a user. The selection unit is configured to select a moving object to be provided to the user according to a satisfied condition of the biological information. The decision unit is configured to acquire priority added to the satisfied condition of the biological information of the user and decide an order of vehicle allocation for the selected moving object according to the priority. The instruction unit is configured to instruct the selected moving object to move according to the positional information.

A second aspect of the disclosure relates to a vehicle allocation service method. The vehicle allocation service method includes, with a management apparatus configured to manage a moving object, acquiring biological information and positional information of a user, selecting a moving object to be provided to the user based on the biological information, acquiring priority added to a satisfied condition of the biological information, deciding an order of vehicle allocation for the selected moving object according to the priority, and giving an instruction for movement according to the positional information.

A third aspect of the disclosure relates to a program. The program causes a computer to implement a function of acquiring biological information and positional information of a user, a function of selecting a moving object to be provided to the user based on the biological information, a function of acquiring priority added to a satisfied condition of the biological information, a function of deciding an order of vehicle allocation for the selected moving object according to the priority, and a function of giving an instruction for movement according to the positional information.

According to the disclosure, it is possible to more rapidly execute countermeasures or actions in emergency.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein:

FIG. 3 is an example (a degree of expansion of a bladder) showing a satisfied condition of biological information according to the first embodiment;

FIG. 4 is an example (a range of a heart rate) showing a satisfied condition of the biological information according to the first embodiment;

FIG. 5 is an example (a range of a body temperature) showing a satisfied condition of the biological information according to the first embodiment;

FIG. 17 is a schematic view showing a vehicle allocation service system according to a fifth embodiment; and FIG. 18 is a schematic view showing a vehicle allocation service system according to a sixth embodiment.

DETAILED DESCRIPTION OF EMBODIMENTS

Figure 1:
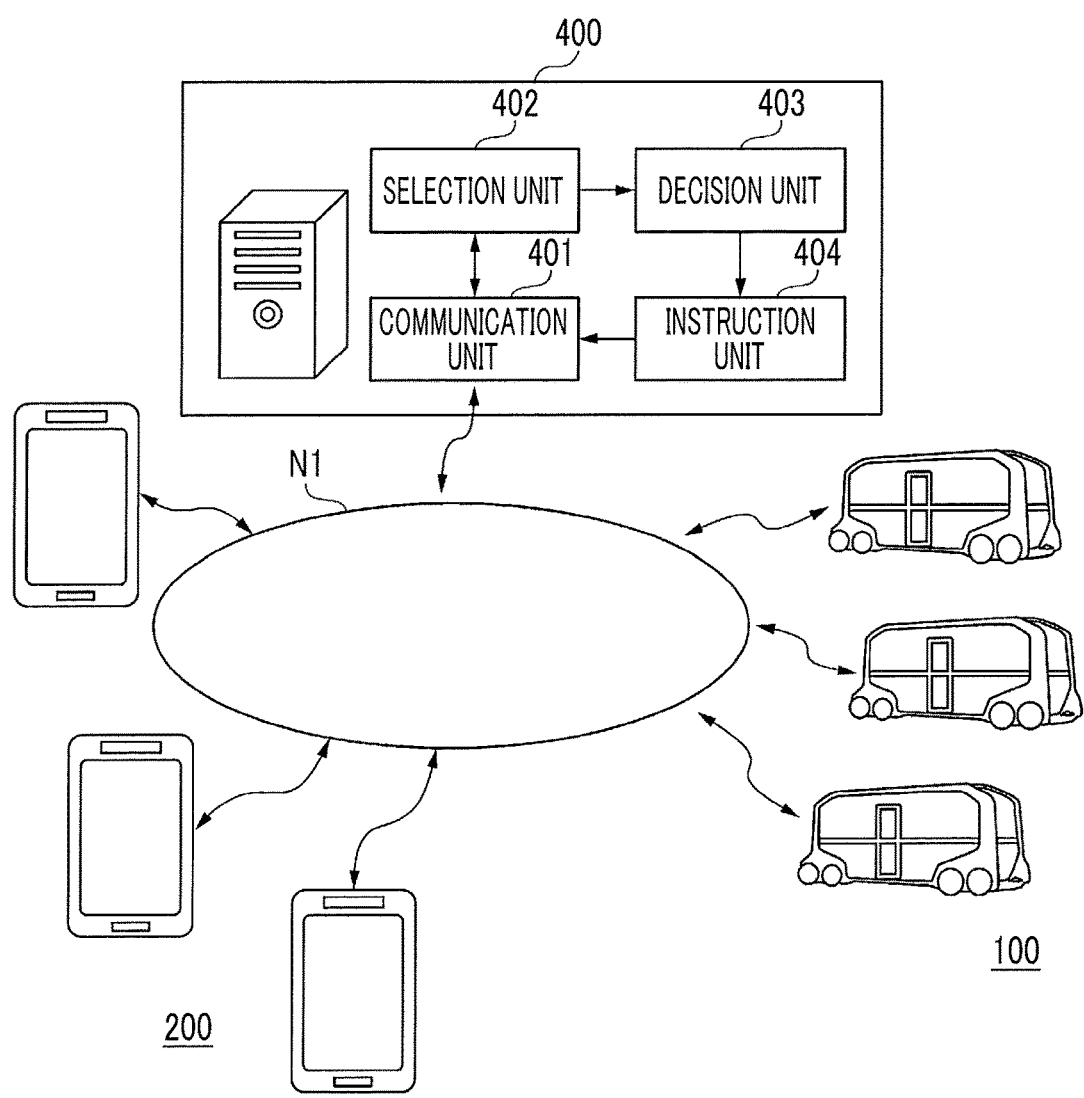
FIG. 1 is a schematic view showing a vehicle allocation service system according to a first embodiment as an embodiment of the disclosure.

Hereinafter, an embodiment of the disclosure will be described in detail referring to the drawings. The configuration of the embodiment is illustrative, and the disclosure is not limited to the configuration of the embodiment.

First Embodiment

FIG. 1 is a schematic view showing a vehicle allocation service system that executes a vehicle allocation service method according to a first embodiment as an embodiment of the disclosure. In FIG. 1, the vehicle allocation service system includes moving objects 100 that are connected to a network N1 to perform communication, user terminals 200 that are connected to the network N1 to perform communication and acquire biological information and positional information of users, and a management server 400. The management server 400 has a selection unit 402 that selects the moving object 100, a decision unit 403 that decides an order of vehicle allocation for the moving object 100, and an instruction unit 404 that gives an instruction for movement according to the positional information.

The biological information is, in principle, a physical quantity obtained by digitalizing a biological phenomenon, such as pulse, blood pressure, breathing, heartbeat, brain wave, and sweating, with a sensor. In a case where a user inputs information regarding a micturition desire or a defecation desire to the user terminal 200, the input information can be regarded as biological information. The positional information of the user is obtained based on global positioning system (GPS) information from a GPS receiver or the like in the user terminal 200 belonging to or carried with the user. In FIG. 1, the user terminal 200 corresponds to an acquisition unit, the selection unit 402 corresponds to a selection unit, the decision unit 403 corresponds to a decision unit, the instruction unit 404 corresponds to an instruction unit, and the management server 400 corresponds to a management apparatus.

The network N1 is, for example, a public communication network, such as the Internet, and a wide area network (WAN) or other communication networks may be employed. The network N1 may include long term evolution (LTE) as a communication network of each mobile phone company, a wireless local area network (LAN: including Wi-Fi), and a wireless communication network and a wired communication network of a private network in a large shopping mall or the like as a commercial facility having an extensive site where a plurality of retail stores and stores of a service industry, such as restaurants, beauty salons, and travel agents, occupy.

The user terminal 200 is, for example, a mobile phone, a smartphone, a portable information terminal, a tablet terminal, a personal computer, or the like. It is desirable that the moving object 100 is an autonomous traveling vehicle that performs autonomous traveling based on a given instruction, autonomous traveling is not a requirement, and the moving object 100 is not necessarily unmanned. For example, movement may be performed by maneuvering of a person. Maneuvering may be maneuvering on the moving object 100 or may be remote control using a remote controller or the like. Alternatively, the moving object 100 may be a ship or an aircraft (an airplane, a helicopter, a drone, or the like).

The management server 400 has a communication unit 401, is connected to other apparatuses through the network N1, and performs communication with the user terminals 200, the moving objects 100, and the like. Communication is performed by, for example, a network interface card (NIC) provided in the management server 400 or a wireless communication circuit for wireless communication. Similarly, each of the user terminals 200 and the moving objects 100 includes a controller or the like having a network function for connection to various networks, such as Ethernet and a wireless LAN.

The management server 400 is a computer that provides a service, and is a computer or software in charge of a function of providing information or a processing result in response to a request from a client. Furthermore, the management server 400 provides functions of a file server, a web server, a print server, and the like. In addition, the functions of both of the server and the client may be placed.

Normally, the management server 400 is mounted with a large number of high-end CPUs, and includes a high-speed bus, peripheral equipment, and the like. Furthermore, various kinds of design for implementing continuous operability are performed. For example, the management server 400 has availability (redundancy of important parts, a RAID, or the like) in a case where failure occurs in a specific part, in addition to reliability (design, manufacturing, and inspection, a main memory with an error detection and correction function, or the like) of an individual part. The management server 400 includes maintainability (various log functions, diagnosis programs, hot swap, or the like) capable of performing diagnosis or replacement of parts in a short time or without stopping. As a shape, a rack-mounted type, a tower type, a blade type, or the like is used.

Specifically, the management server 400 includes a processor, such as a CPU or a digital signal processor (DSP), a memory (not shown), such as a random access memory (RAM) or a read only memory (ROM), and an auxiliary storage device, such as an erasable programmable ROM (EPROM) or a hard disk drive (HDD). The auxiliary storage device stores an operating system (OS), various programs, various tables, and the like. The processor loads the programs stored in the auxiliary storage device to a work area of the memory and executes the programs. With the execution of the programs, various kinds of processing or operations are executed, whereby functions conforming to predetermined purposes are implemented.

Figure 2:
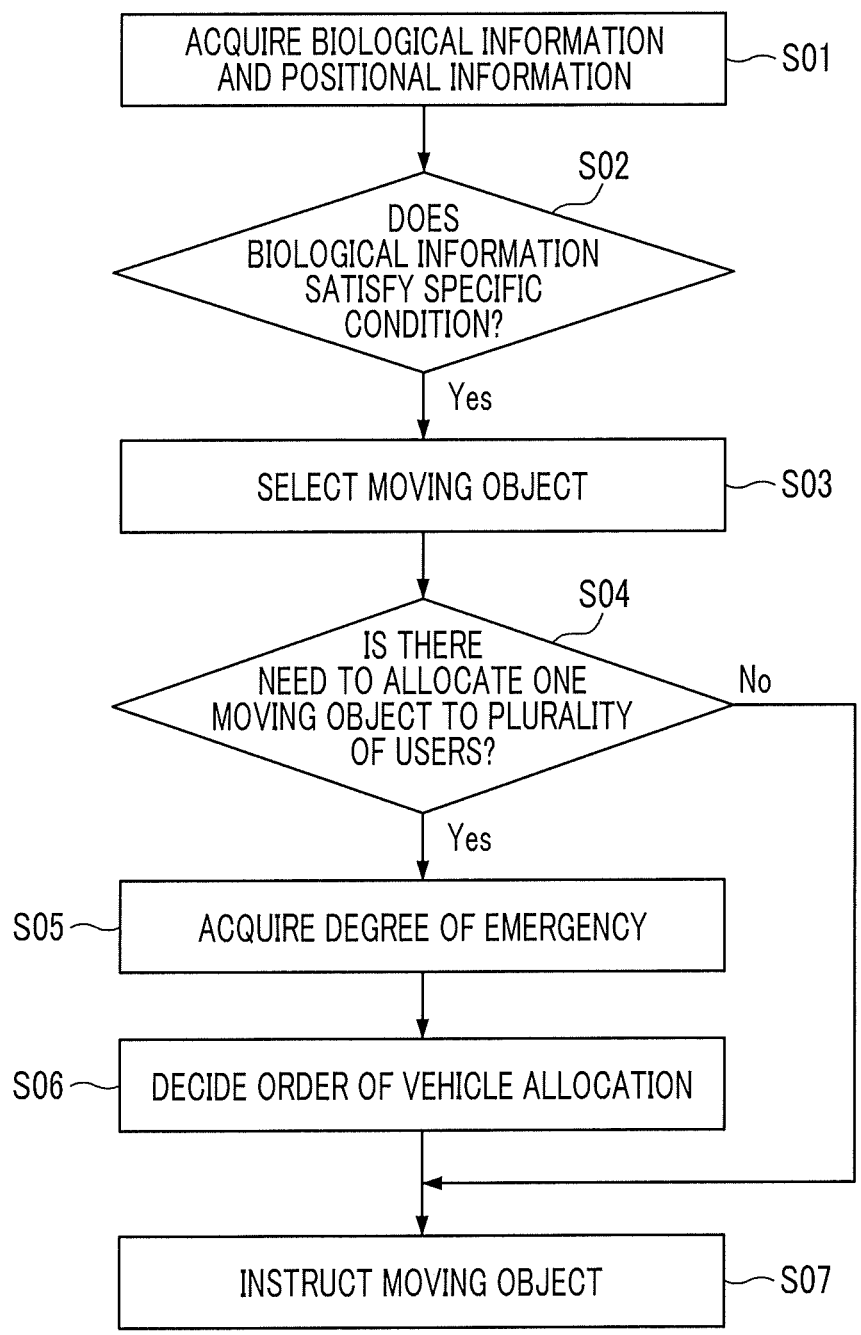
FIG. 2 is a flowchart showing a procedure for deciding vehicle allocation according to the first embodiment.

FIG. 2 is a flowchart showing a procedure for deciding vehicle allocation for the moving object 100 according to a degree of emergency with the management server 400. The biological information and the positional information are acquired by the user terminal 200 or are acquired from various sensors through the user terminal 200, the network N1, and the communication unit 401 (S01). Next, the following processing is primarily executed by the selection unit 402. For example, the selection unit 402 defines the correspondence relationship between a numerical range of the biological information and the kind of the moving object 100, and determines whether or not the biological information of the user satisfies a specific condition (S02). Then, the selection unit 402 selects a moving object to be provided to the user according to a satisfied condition of the biological information. Specifically, the decision unit 403 selects the moving object 100 of a kind or having a function corresponding to a predetermined specific condition (S03). The selection unit 402 confirms whether or not a plurality of users demands, that is, whether or not the biological information and the positional information are input from a plurality of user terminals 200 and determines whether or not there is a need to allocate one moving object 100 (S04)

Here, a procedure for detecting a micturition desire as a swelling of a bladder, that is, a degree of expansion of the bladder with an ultrasonic sensor will be described. For example, in regard to the micturition desire, it is assumed that a user to be a subject mounts an ultrasonic sensor incorporated into a wearable device on a lower abdominal region. The decision unit 403 monitors and analyzes movement in a body based on a signal from the ultrasonic sensor and predicts a timing of micturition or defecation. A bladder capacity indicates the amount of urine that can be accumulated in the bladder, and indicates the amount that a person has a micturition desire. The micturition desire is divided into an incipient micturition desire, a normal micturition desire, a strong micturition desire, and the like. In the incipient micturition desire that is an initial slight micturition desire, it is possible to consciously suppress micturition. FIG. 3 is an example showing a satisfied condition of the biological information. As the satisfied condition of the biological information, an example where "a degree of emergency" is added to "the degree of expansion of the bladder" is shown. A function needed as the moving object 100 is a toilet function, and a toilet is selected as the kind of the moving object. The degree of emergency can be referred to as an example of priority.

As an example of the degree of emergency, as shown in FIG. 3, a case where "the degree of expansion of the bladder" is 100 to 120% is a normal micturition desire, and an arrival time is determined to be within 30 minutes. Similarly, in a case where "the degree of expansion of the bladder" is 120 to 150%, priority (the arrival time is within 15 minutes) is given, and in a case where "the degree of expansion of the bladder" is equal to or greater than 150%, the highest priority (the arrival time is within three minutes) is given.

The numerical range of "the degree of expansion of the bladder" and the degree of emergency of FIG. 3 are illustrative, and are not necessarily accurate. A timing of the toilet has an individual difference, and it is desirable that an excretion time is recorded individually, such that a timing of excretion is learned. Since the more the user goes to the toilet, the more the accuracy of the presence or absence of the micturition desire and the correspondence of the numerical range of "the degree of expansion of the bladder" and the degree of emergency is improved, it should suffice that a function of machine learning is mounted in the management server 400 or the user terminal 200. In addition, it is desirable to construct a system by analyzing anthropometric surveys of micturition and defecation patterns of a large number of users and trends.

In a case where the number of moving objects 100 to be allocated is smaller than the number of users, the decision unit 403 acquires the degree of emergency (S05), and decides an order (the priority of each user) of vehicle allocation for the moving object 100 selected by the selection unit 402 to the user according to the degree of emergency (S06). Then, the instruction unit 404 performs scheduling according to the decided priority to instruct the moving object 100 to move according to the positional information of the user (S07). Of course, in a case where a sufficient number of moving objects 100 can be allocated to a plurality of users, the instruction unit 404 gives an instruction for movement regardless of the degree of emergency. For example, in a case where determination is made that the user has a micturition desire or a defecation desire under the satisfied condition of the biological information of the user, the selection unit 402 selects the moving object 100 having a toilet function, and the instruction unit 404 gives an instruction for movement to the moving object 100 with the selection of the selection unit 402.

FIG. 4 is an example where the kind of a moving object is determined with respect to a satisfied condition of a range of a pulse rate (heart rate), and FIG. 5 is an example where the kind of a moving object is determined with respect to a range of a body temperature. Since the pulse rate can be referred to as a heart rate in a similar sense, and the numerical values of the pulse rate and the heart rate have the same value, the pulse rate and the heart rate are generally synonyms. The pulse rate has a slightly different normal value by sex or age, and normally, in a case of a general adult, 60 to 100 beats per minute is a normal value.

A case where the heart rate for one minute exceeds 100 beats is referred to as a frequent pulse, and as a cause for a rapid pulse, a dominant operation of a sympathetic nerve is considered. The heart rate increases in a so-called "nervous scene" or "excited state", and in a case where the user feels strong stress mentally, the sympathetic nerve is excited and the pulse rate increases. In a case where a myocardium is contracting disorderly, the heartbeat suddenly increases to be equal to or higher than 200, causing ventricular fibrillation that is a kind of irregular pulse and a ventricle of a heart shakes slightly.

A case where the heart rate for one minute is less than 60 beats is referred to as an infrequent pulse, and in a case where a parasympathetic nerve is dominant, the pulse rate decreases. In a case where the infrequent pulse suddenly occurs, the body may be in an oxygen deficient state, and since the amount of blood sent to the whole body decreases, in a severe case, the user may suffer from loss of consciousness or the like.

Accordingly, the selection unit 402 selects a kind in consideration of the degree of emergency as the moving object 100. That is, as shown in FIG. 4, in a case where the range of the heart rate is 0 to 60 beats per minute, the selection unit 402 selects an ambulance with a physician. The ambulance with a physician is a vehicle that loads medical machines, such as an artificial heart massager, an artificial respirator, and an inspection device, and is sent directly to a site in a state in which a physician, a nurse, and the like board the vehicle. In a case where the range of the heart rate is 60 to 100 beats per minute, the selection unit 402 selects a general vehicle having no special equipment. Similarly, in a case where the range of the heart rate is 100 beats per minute, the selection unit 402 selects an ambulance that loads a stretcher for accommodating a sick and wounded person, medicines for treatments, medical equipment, such as an AED and an electrocardiogram monitor, an oxygen cylinder, and the like.

In regard to the range of the body temperature, a general adult has a normal value of 36.6 to 37.2° C., and an old person has a normal value lower than the normal value of the general adult by 0.2 to 0.5° C. In a state in which the range of the body temperature is equal to or lower than 34° C., degradation of a viscera function or damage to a brain is also considered, and dizziness occurs or breathing becomes painful. A state in which the range of the body temperature is about 34° C. is near a state like hypothermia, and causes various symptoms, such as abdominal pain, diarrhea, and dizziness. A state in which the range of the body temperature is in the latter half of about 37° C. and exceeds 38° C. is a fever, and exhibits symptoms, such as rapid heartbeat, chillness and coldness, muscle pain, anorexia, and rapid breathing. A state in which the body temperature exceeds 40° C. is an abnormal high temperature. In this state, a body temperature management system of the brain falls into an uncontrollable state, symptoms, such as bleeding, dark urine, and unconsciousness, appear. This is caused by fit, paralysis, tumor, encephalitis, serious internal bleeding, or the like.

Accordingly, the decision unit 403 selects a kind in consideration of the degree of emergency as the moving object 100. That is, as shown in FIG. 5, in a case where the range of the body temperature is equal to or lower than 34° C., an ambulance with a physician or a helicopter is selected. In a case where the range of the body temperature is 34 to 36° C., an ambulance is selected, in a case where the range of the body temperature is 36 to 38° C., a general vehicle is selected, in a case where the range of the body temperature is 38 to 40° C., an ambulance is selected, and in a case where the range of the body temperature is equal to or higher than 40° C., an ambulance with a physician or a helicopter is selected.

The numerical ranges of FIGS. 4 and 5 are illustrated similarly to FIG. 3, and are not necessarily accurate. It is desirable that the numerical ranges are determined by a learning system 412 and an intelligence system 411 (see FIG. 6) based on a rule of thumb and analysis of results of a large number of users and trends. The numerical ranges are not simply determined as threshold values. Accordingly, the decision unit 403 may determine a membership function in fuzzy logic with respect to the biological information, in the examples of FIGS. 3, 4, and 5, the degree of expansion of the bladder, the range of the heart rate, and the range of the body temperature, may substitutes quantities represented by the numerical values using the membership function, and may decide the kind of the moving object and the degree of emergency according to a fuzzy rule. Of course, in deciding the kind of the moving object and the degree of emergency, it is desirable that the decision unit 403 may combine a plurality of pieces of biological information and may perform fuzzy inference to decide the kind of the moving object and the degree of emergency based on a complicated correspondence relationship. The conditions of the biological information shown in FIGS. 3 to 5, that is, the relationships between the degree of expansion of the bladder, the range of the heart rate, the range of the body temperature, and the like and the kind of the moving object, the degree of emergency, and the like can be incorporated into a computer program that is executed by a CPU executing processing as the decision unit 403 or the instruction unit 404 and is mounted in a memory. For example, the management server 400 may hold the relationships shown in FIGS. 3 to 5 as a knowledge based described in "If condition then processing 1 else processing 2".

According to the above-described embodiment, the vehicle allocation service system selects the moving object 100 according to the degree of emergency with respect to the satisfied condition of the biological information of the user and decides the order of vehicle allocation, that is, the priority of the user according to the degree of emergency. For this reason, the vehicle allocation service system can cope with demands from a plurality of users in emergency correctly in a possible range such that the satisfaction of the users is obtained and can execute actions.

Figure 6:
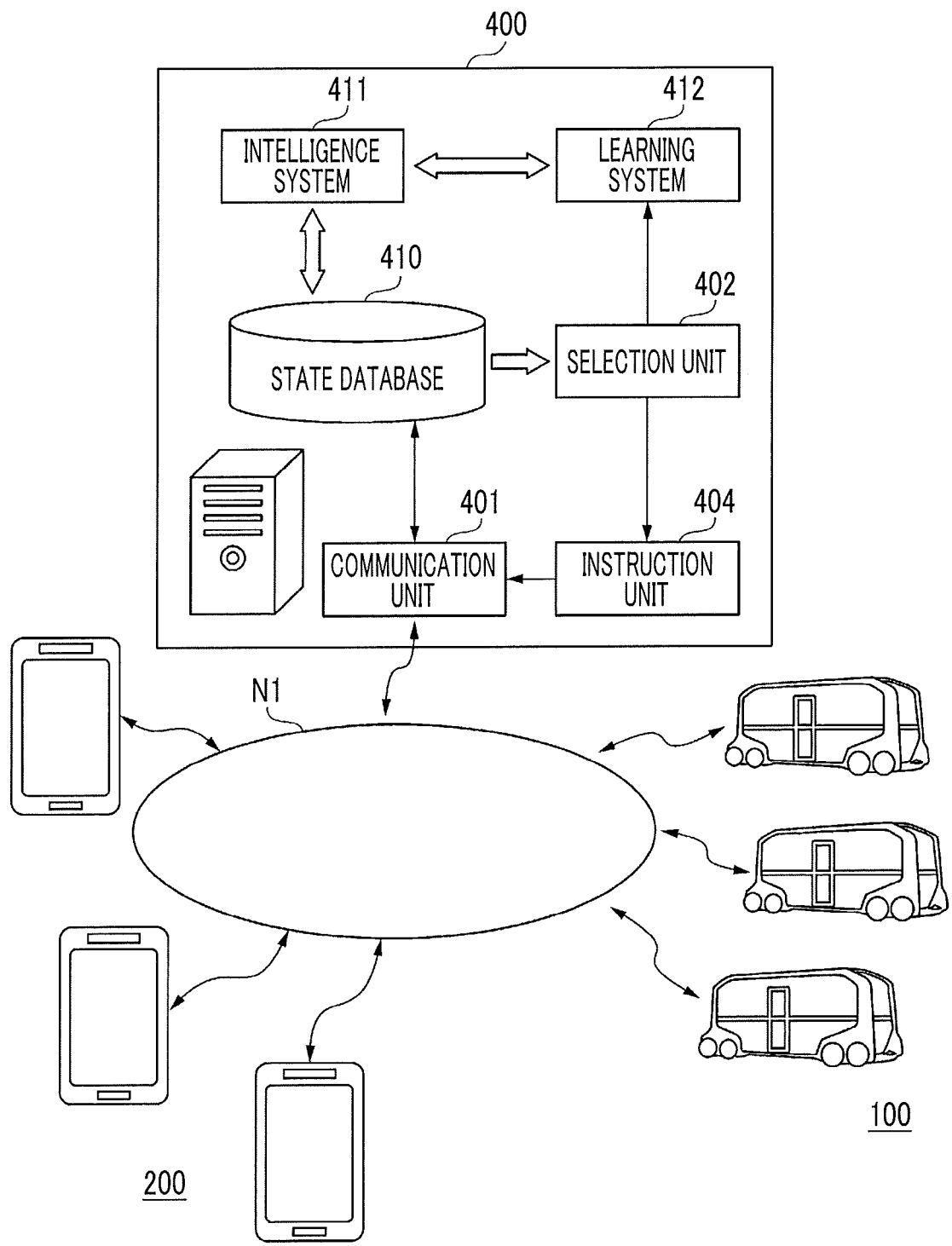
FIG. 6 is a schematic view showing a vehicle allocation service system according to a modification example of the first embodiment.

FIG. 6 is a schematic view showing a vehicle allocation service system according to a modification example of the first embodiment of the disclosure. In the above-described first embodiment, the relationships between the conditions of the biological information illustrated in FIGS. 3 to 5, the degree of expansion of the bladder, the range of the heart rate, the range of the body temperature, and the like and the kind of the moving object, the degree of emergency, and the like are incorporated in the decision unit 403 or the instruction unit 404. Alternatively, the relationship between the conditions of the biological information illustrated in FIGS. 3 to 5 and the kind of the moving object, the degree of emergency, and the like may be stored as a state database 410 in an auxiliary storage device readable by the management server 400 or a database server or the like on a network. In this case, it can be said that the state database stores the biological information and the kind of the moving object to be provided to the user in association with each other. The management server executes processing using the state database 410, whereby it is possible to easily adjust the relationship between the conditions of the biological information and the kind of the moving object, the degree of emergency, and the like in the vehicle allocation service system. For example, in a case where the state database 410 is rewritable by the management server 400, the management server 400 may receive feedback of the satisfaction of the user or the like from a result of information processing of FIG. 2 and may update the conditions of the biological information.

Second Embodiment

Figure 7:
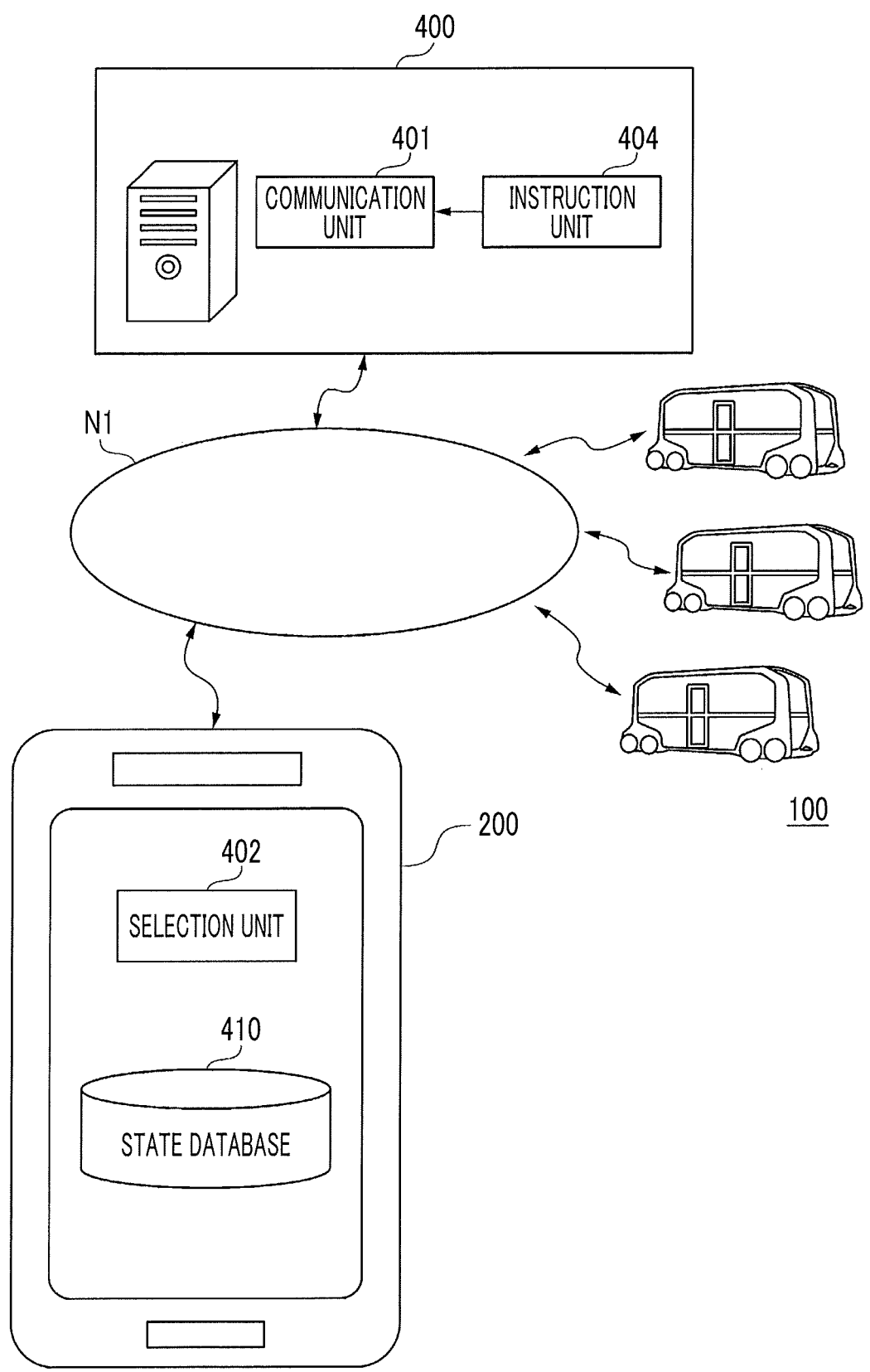
FIG. 7 is a schematic view showing a vehicle allocation service system according to a second embodiment.
Figure 8:
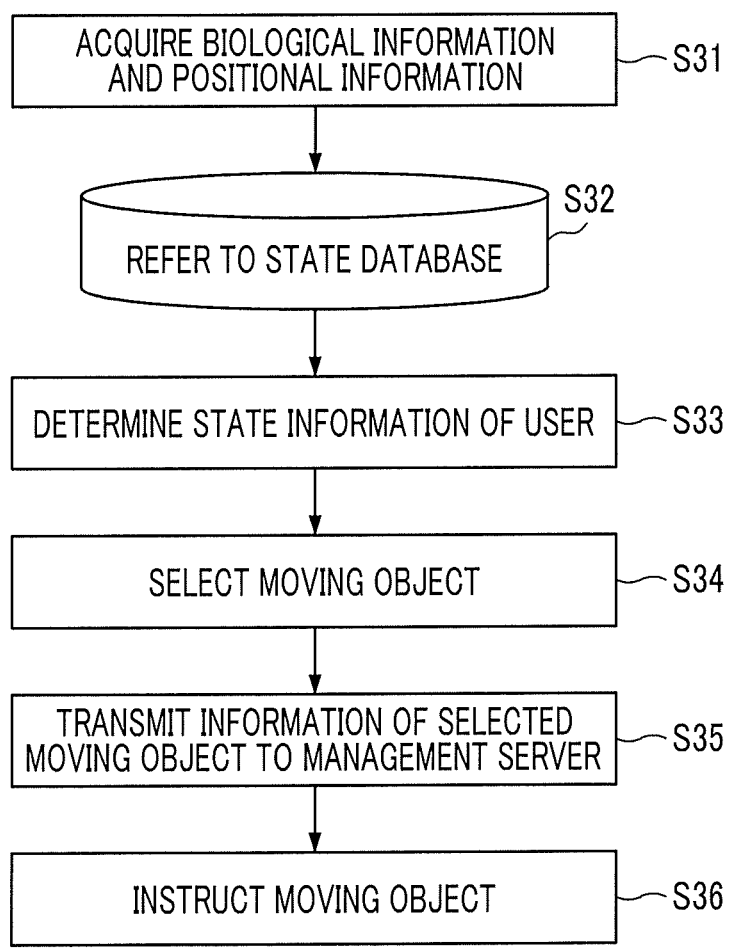
FIG. 8 is a flowchart showing a procedure for deciding vehicle allocation according to the second embodiment.

FIG. 7 is a schematic view showing a vehicle allocation service system according to a second embodiment of the disclosure. A difference from the first embodiment shown in FIG. 6 is that the state database 410 and the selection unit 402 are provided in the user terminal 200, and information of the moving object 100 selected by the user terminal 200 is transmitted to the communication unit 401 of the management server 400. FIG. 8 is a flowchart showing a procedure for deciding vehicle allocation, and shows a procedure until the instruction unit 404 gives an instruction for movement to the moving object 100 selected by the selection unit 402.

The user terminal 200 acquires the biological information and the positional information from various sensors (S31). Various sensors may be accessible from the user terminal 200 through wireless communication or may be embedded in the user terminal 200. The user terminal 200 refers to the state database 410 based on the acquired biological information (S32), and determines state information of the user (S33). With this, the user terminal 200 determines whether or not the acquired biological information of the user satisfies a condition. The selection unit 402 of the user terminal 200 selects the moving object 100 of a kind or having a function corresponding to the condition based on the state database 410 (S34). The user terminal 200 transmits information indicating the selected moving object 100, that is, a serial number and a name to the management server 400 through the communication unit 401 (S35). The management server 400 gives an instruction for movement to the moving object 100 conforming to the transmitted information among the moving objects 100 being managed by the management server 400 (S36).

Since the user terminal 200 does not have high performance compared to the management server 400 mounted with the high-end CPU, the state database 410 may be specified while omitting a part from the state database 410 described referring to FIG. 6. The state database 410 may be simply data or a data string determining the correspondence relationship between the range of the heart rate or the range of the body temperature and the kind of the moving object 100 shown in FIG. 4 or 5.

The user terminal 200 may use the state database 410 in the management server 400 in combination with the second embodiment shown in FIG. 6. Alternatively, the user terminal 200 may perform communication with the management server 400 in advance to download the latest state database 410.

According to the above-described embodiment, the system configuration is simplified, and the system can be constructed even in a form in which a dedicated application is installed in a smartphone. In a small-scale site, a building, or the like, the instruction unit 404 of the management server 400 may be omitted, and an instruction for movement may be given directly from the user terminal 200 to the moving object 100. For example, this is suitably applied to a case where a fire extinguisher or an AED is provided as a function provided in the moving object 100.

Third Embodiment

Figure 9:
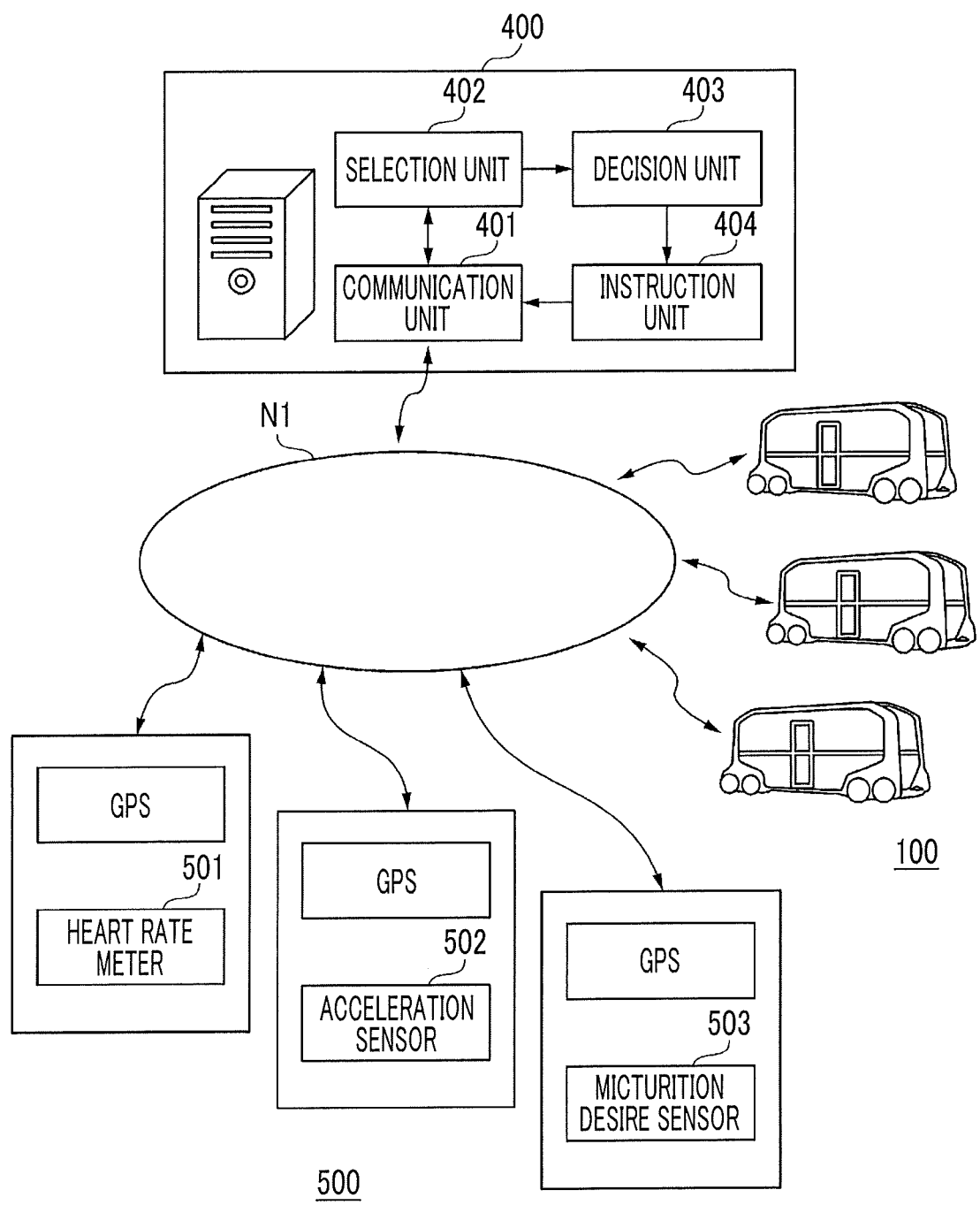
FIG. 9 is a schematic view showing a vehicle allocation service system according to a third embodiment.
Figure 10:
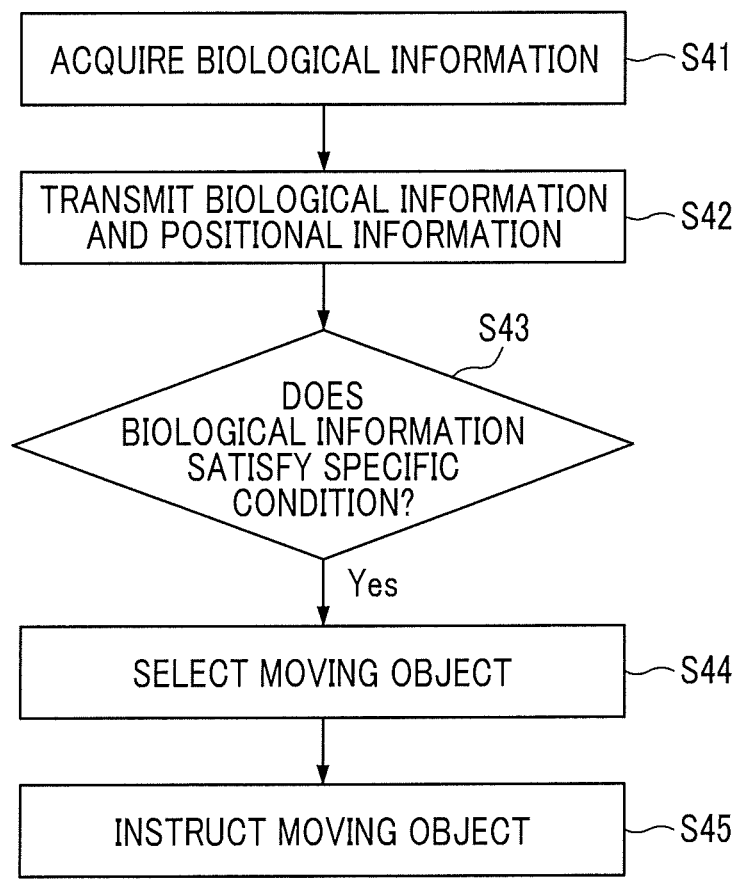
FIG. 10 is a flowchart showing a procedure for deciding vehicle allocation according to the third embodiment.

FIG. 9 is a schematic view showing a vehicle allocation service system according to a third embodiment of the disclosure. A difference from the embodiment shown in FIG. 1 is that the vehicle allocation service system of the embodiment has a biosensor 500 including a communication function and a GPS function instead of the user terminal 200. FIG. 10 is a flowchart showing a procedure for deciding vehicle allocation, and shows a procedure from when biological information is acquired by the biosensor 500 until the instruction unit 404 gives an instruction for movement to the moving object 100 selected by the selection unit 402.

The biological information and the positional information are acquired by the biosensor 500 (S41). Next, as an example of FIG. 9, a heart rate from a heart rate meter 501, acceleration information indicating an acceleration acquired by an acceleration sensor 502, numerical data of the degree of expansion of the bladder by a micturition desire sensor 503 are transmitted to the management server 400 by a communication unit and a GPS receiver compounded in the biosensor 500 (S42). The micturition desire sensor has an ultrasonic sensor mounted on the lower abdominal region as in the first embodiment. A plurality of biosensors 500 may be provided as in FIG. 9 or solely one biosensor 500 may be provided and may function alone.

The selection unit 402 of the management server 400 defines the correspondence relationship between a numerical range of the biosensor 500 and the kind of the moving object 100 as in the first embodiment and determines whether or not the biological information of the user satisfies a condition (S43). The selection unit 402 selects the moving object 100 of a kind or having a function corresponding to a predetermined condition (S44). Then, the instruction unit 404 instructs the moving object 100 to move according to the positional information of the biosensor 500 (S45).

As described above, for example, in a case where determination is made that the user has a micturition desire or a defecation desire under a condition of the degree of expansion of the bladder obtained by the micturition desire sensor 503, the management server 400 selects the moving object 100 having a toilet function and gives an instruction for movement. Furthermore, the management server 400 determines whether the user falls down or does not move based on the heart rate from the heart rate meter and the acceleration information from the acceleration sensor, selects the moving object 100 with an AED, and gives an instruction for movement. Alternatively, the biosensor 500 may transmit solely the positional information to the management server 400, and an instruction for movement may be given directly from the biosensor 500 to the moving object 100. According to the above-described embodiment, since the system configuration is simplified, this is suitably applied to a case where a specific function is specialized.

Fourth Embodiment

Figure 11:
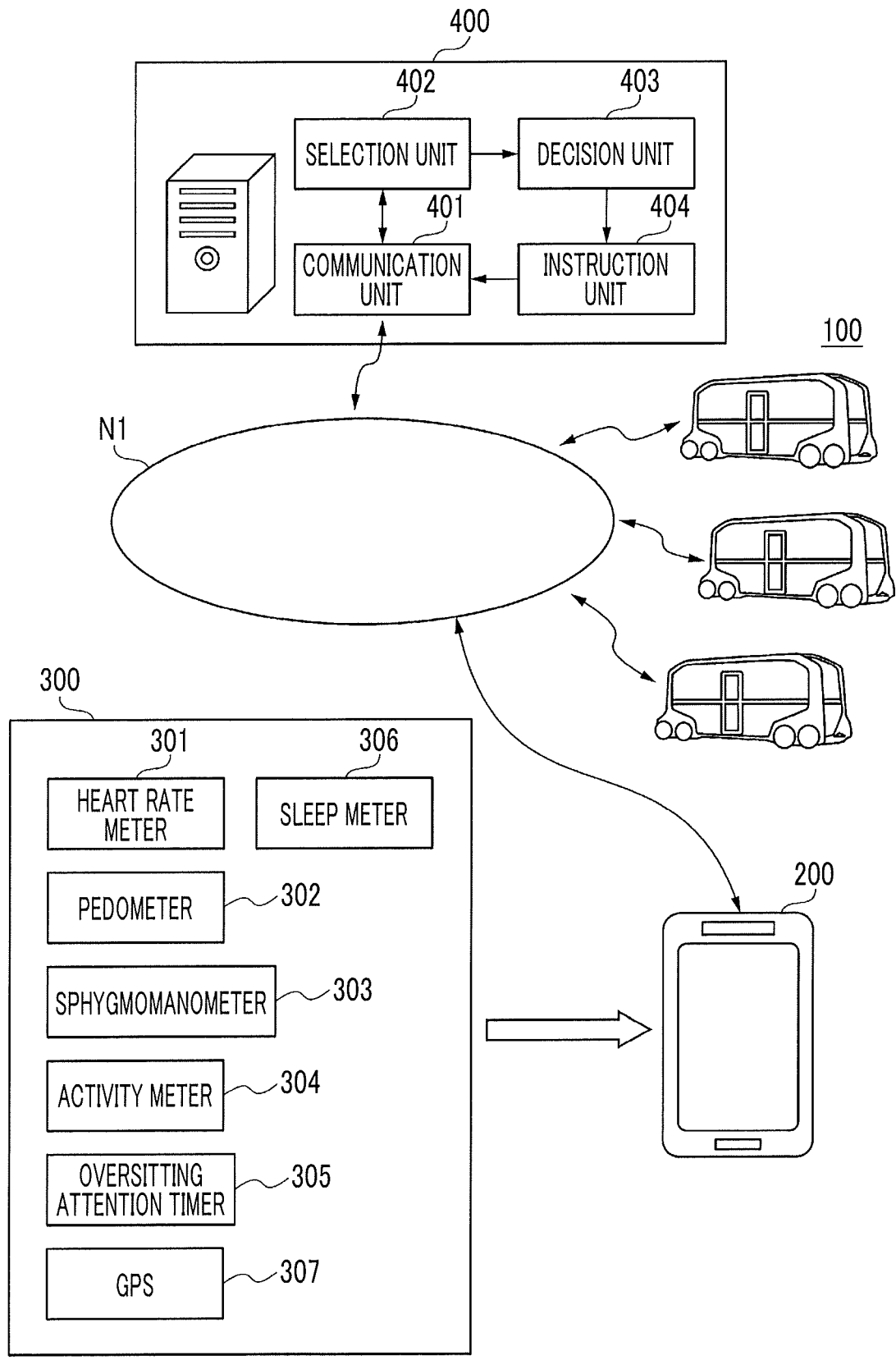
FIG. 11 is a schematic view showing a vehicle allocation service system according to a fourth embodiment.
Figure 12:
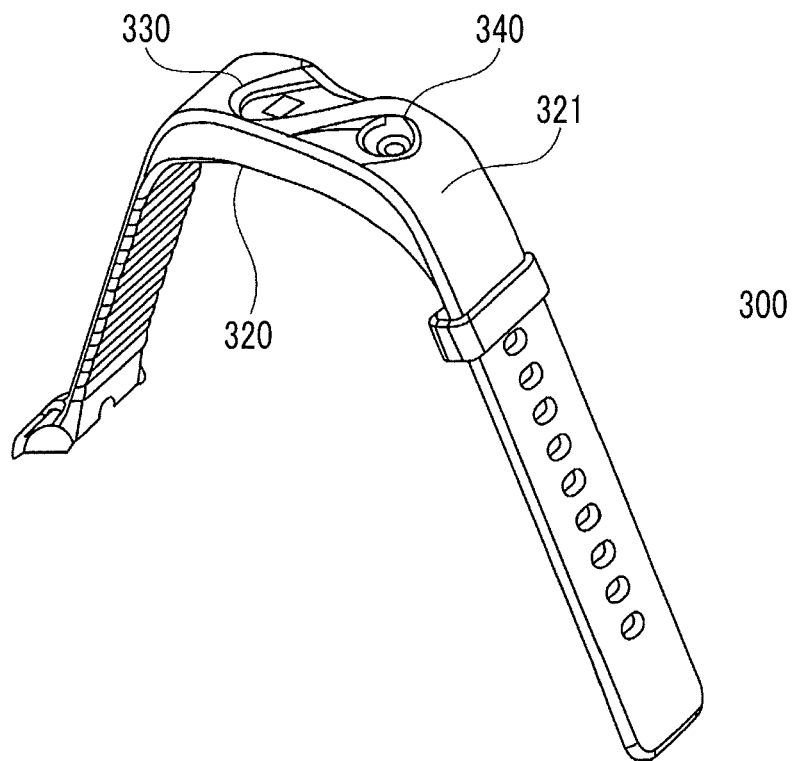
FIG. 12 is a perspective top view of a smartwatch according to the fourth embodiment.
Figure 13:
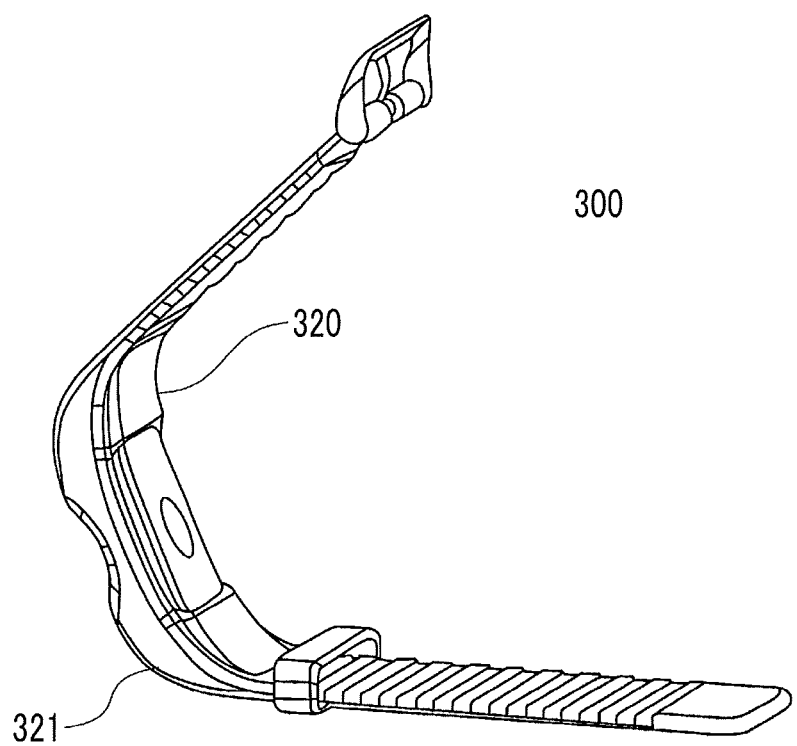
FIG. 13 is a perspective rear view of the smartwatch according to the fourth embodiment.

FIG. 11 is a schematic view showing a vehicle allocation service system according to a fourth embodiment of the disclosure. A difference from the embodiment shown in FIG. 1 is that the biological information is acquired using a smartwatch 300 and the user terminal 200 is a smartphone. The smartwatch 300 normally has a wristwatch function and a GPS receiver 307, is provided with a CPU therein, and has a function of performing communication with the user terminal 200 according to a wireless communication protocol, such as Bluetooth (Registered Trademark). In the smartwatch 300, as sensors, a pressure sensor, an optical sensor, a motion sensor, and the like are incorporated. For this reason, the smartwatch 300 has functions as an activity meter 304, a pedometer 302, a heart rate meter 301, a sphygmomanometer 303, a sleep meter 306, an oversitting attention timer 305, and the like. FIG. 12 is a perspective top view of the smartwatch 300, and FIG. 13 is a perspective rear view of the smartwatch 300. The smartwatch 300 is a wearable device that is worn on a hand or an arm for use in a form of a wristwatch belt, a necklace, a wristband, a bracelet, an arm cover, or the like.

In FIGS. 12 and 13, the smartwatch 300 includes an inside 320 and an outside 321 that are connected to each other. The inside 320 is adhered to the skin. In a measurement unit 330, as sensors, a pressure sensor, an optical sensor, a motion sensor, an electrode, and the like are incorporated. Reference numeral 340 denotes a body temperature sensor. The measurement unit 330 can detect heartbeat, blood pressure, vascular elasticity, and the like. For example, in a case where the skin is irradiated with light having a specific wavelength, the optical sensor receives light reflected from the body surface or transmitted through a part of the body. The intensity of the received light reflects the quantity of light absorption of a blood component, and a signal of a photoelectric plethysmogram can be obtained. The measurement unit 330 can calculate blood pressure using a sphygmogram feature quantity. In a case where myocardial cell is polarized every heartbeat, a weak electrical change occurs in the skin surface; and thus, the heartbeat can be not only detected by the pressure sensor or an optical sensor, but also can be measured by the electrode.

As described above, the user can wear the smartwatch 300 as a wearable device, can measure an electrocardiogram, vascular elasticity, blood pressure, blood oxygen, heartbeat, and a body temperature at any time, and can count the number of steps. Then, the biological information may be transmitted to the user terminal 200 as a smartphone or the management server 400 and may be stored and updated continuously, intermittently, regularly, or at any desired frequency or time interval. In addition, the user terminal 200 obtains common health data or activity amount based on the stored biological information. Then, the user terminal 200 or the management server 400 may select the moving object 100 based on the health data or the activity amount. Alternatively, the user terminal 200 or the management server 400 may determine the state information of the user, that is, a micturition desire state, the kinds of various diseases, a state of an injury, the degree of emergency, and the like based on normal health data or activity amount to select the moving object 100.

The health data may include any kinds of data associated with human health, such as a body weight, a heart rate, blood pressure, a blood glucose level, medication compliance, and an activity amount. The activity meter 304 that measures the activity amount has a shape or a way to use similar to the pedometer 302. While the pedometer 302 measures walking activity and displays the number of steps or calorie consumption during walking, the activity meter 304 measures various kinds of activity, such as housework or deskwork, as well as walking and obtains daily total calorie consumption. For example, an exercise amount indicating the activity amount is a unit of an amount of physical activity, and the strength and time of exercise are calculated by multiplying the amount and time of exercise.

A procedure for deciding an order of vehicle allocation for the moving object 100, and the like are the same as those in the first embodiment described above. According to the above-described embodiment, various systems can be constructed in such a form that a dedicated application is installed on the user terminal 200. The instruction unit 404 of the management server 400 may be omitted, and an instruction for movement may be given directly from the user terminal 200 to the moving object 100.

In recent years, a large facility, such as a shopping mall, a large park, or a large recreation center is opened at each place, and commercial facilities including a plurality of retail stores or various stores, such as restaurants, famous specialty stores in particular fields, service stores, and amusement facilities, occupy in an extensive site. In the facilities, for example, in regard to demand of a visitor for a toilet, a toilet is not installed in an individual facility. Instead, a place is appropriately determined and a toilet is installed. However, a user who uses a facility does not always know the installation place of the toilet. Accordingly, in emergency, the user is really confused. Besides the toilet, in regard to an AED corresponding to a sudden illness or an injury, a fire extinguisher needed for early fire extinguishing, or the like, a similar situation occurs.

Figure 14:
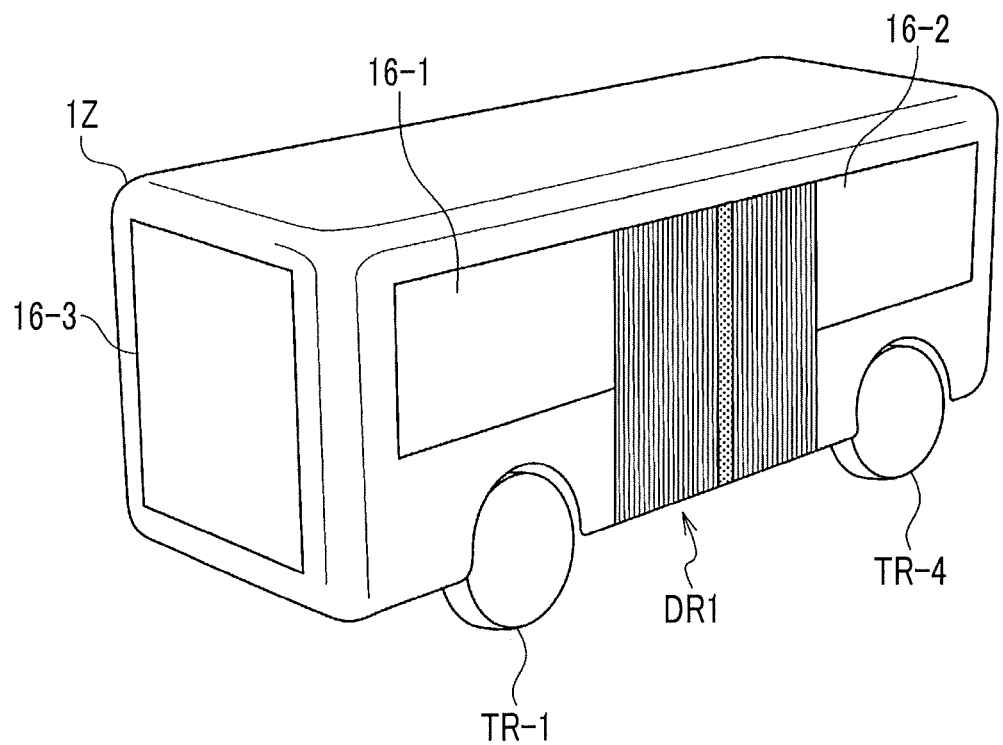
FIG. 14 is a perspective view showing the appearance of an e-pallet (moving object)
Figure 15:
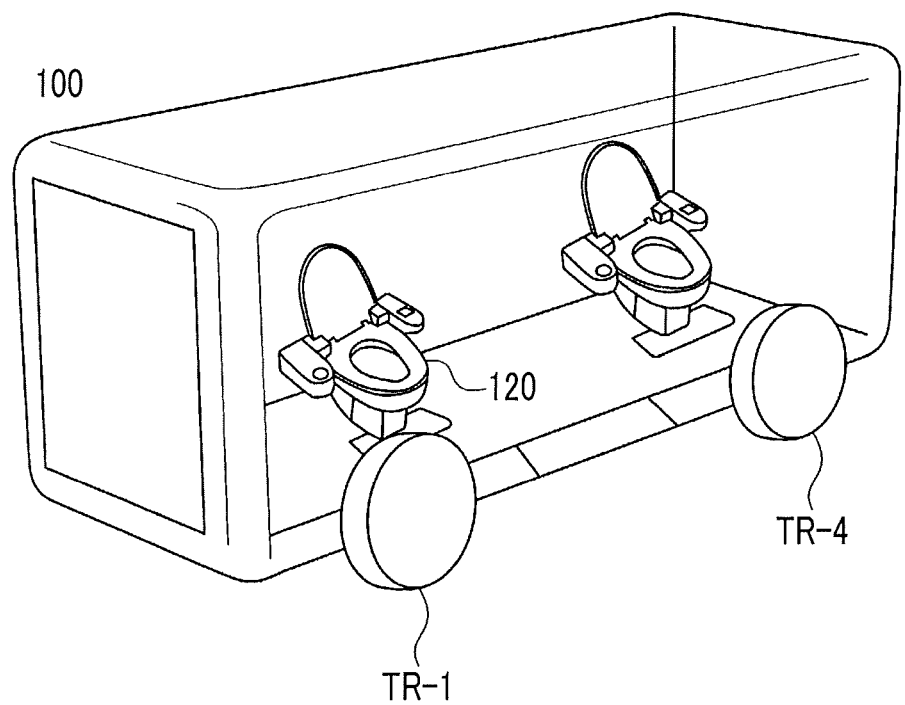
FIG. 15 is a perspective view showing the inside of a mobility toilet (moving object)

In regard to the above-described demand, the vehicle allocation service system of the embodiment provides mobility to the toilet, the AED, the fire extinguisher, or the like, and uses, as the moving object 100, an e-pallet as a next generation EV dedicated for a mobility service utilizing an autonomous driving technique. That is, the vehicle allocation service system of the embodiment implements a mobility toilet (anywhere toilet), a mobility AED, a mobility hospital, a mobility clinic, an MRI, or a mobility CT. The e-pallet is an autonomous traveling vehicle, and there are three sizes of vehicles that are different in total length depending on the number of trunk units. A vehicle of a small size is suitably used in a large facility, and is mounted with a facility according to a use or a function in a flat space adopted low-floor box type barrier-free design. FIG. 14 is a perspective view showing the appearance of an e-pallet, and FIG. 15 is a perspective view showing the inside of a mobility toilet.

The e-pallet (moving object 100) has a box-shaped body 1Z, and four wheels TR-1 to TR-4 provided in front and rear in a moving direction on both sides of a lower portion of the body 1Z. The four wheels TR-1 to TR-4 are coupled to a drive shaft and are driven by a motor for driving. The moving direction of the four wheels TR-1 to TR-4 during traveling is displaced relatively with respect to the body 1Z by a motor for steering, whereby the moving direction is controlled.

As in FIG. 14, displays 16-1 to 16-3 are fixed to the outer wall of the body 1Z. The displays 16-1 to 16-3 are, for example, liquid crystal displays, electroluminescence panels, or the like. FIG. 15 illustrates the configuration of the inside of the body 1Z. In a case where the user uses the mobility toilet, the user opens a door DR1, enters a room, and uses a toilet 120. Though not shown in FIG. 15, a wall is provided between two toilet bowls, and two rooms are formed. The door DR1 is separated into two parts, and the two rooms are opened and closed individually. Similarly, the mobility AED is mounted with an AED apparatus, the mobility MRI is mounted with an MRI apparatus, and the mobility CT is mounted with a CT apparatus. Of course, the mobility toilet, the mobility AED, the mobility MRI, the mobility CT, and the like may be mounted in the e-pallet (moving object 100) in combination.

Figure 16:
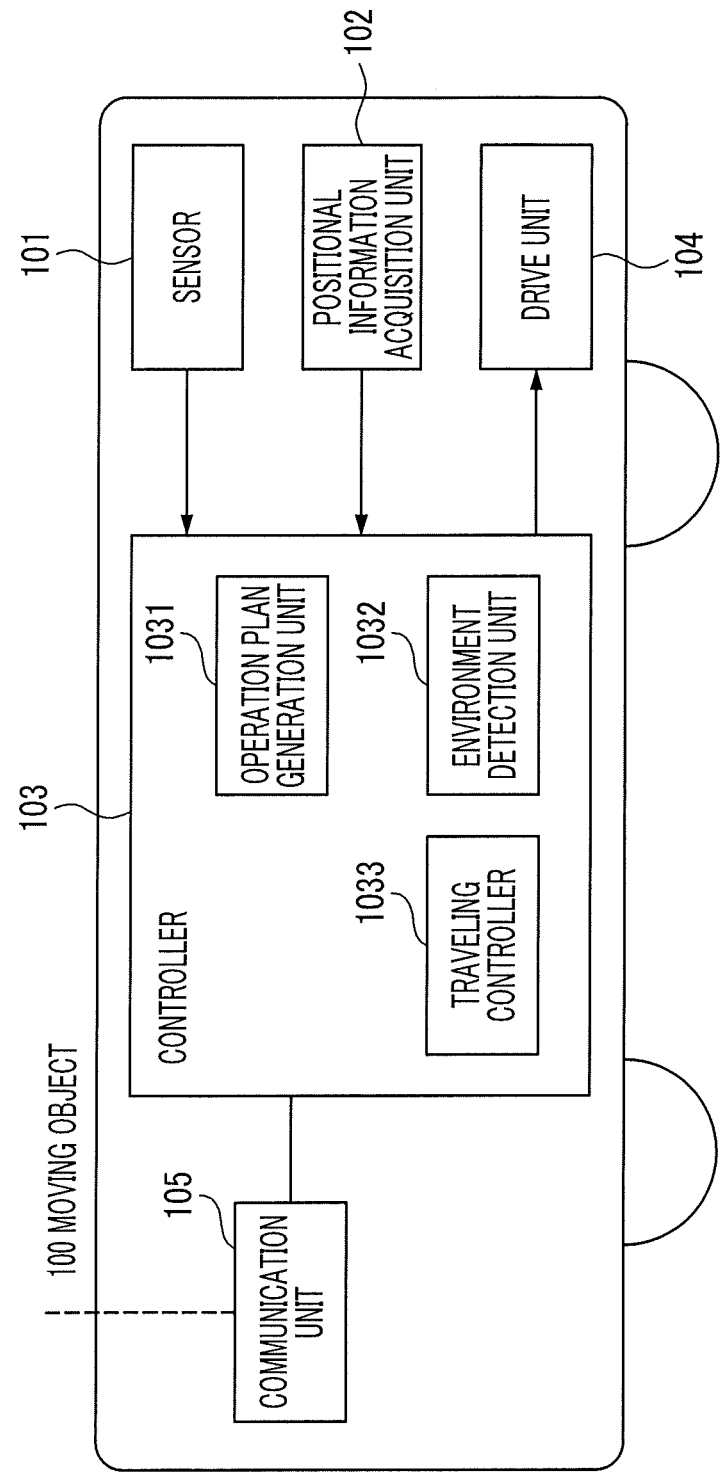
FIG. 16 is a block diagram of a main part of the e-pallet (moving object)

FIG. 16 is a block diagram of a main part of the e-pallet (moving object 100). A controller 103 corresponds to an instruction acquisition unit and a movement controller, and the controller 103 is a computer that controls the moving object 100 based on information acquired from a sensor 101 or a positional information acquisition unit 102. The controller 103 includes a CPU, a memory, and an auxiliary storage device (hard disk or the like), and the CPU loads a program stored in the auxiliary storage device to the memory and executes the program, whereby functions for executing various kinds of processing are implemented. As a specific example of various kinds of processing, the controller 103 operates as an operation plan generation unit 1031, an environment detection unit 1032, and a traveling controller 1033.

The e-pallet (moving object 100) travels according to an instruction acquired from the management server 400. The e-pallet generates a traveling route based on an instruction acquired through the network N1 and performs autonomous traveling while sensing surroundings, thereby traveling on a road or a passage in a large facility. The e-pallet (moving object 100) includes the sensor 101, the positional information acquisition unit 102, the controller 103, a drive unit 104, and a communication unit 105. In addition, the e-pallet (moving object 100) is mounted with a battery (secondary battery) and operates with electric power supplied from the secondary battery.

The sensor 101 performs sensing of the surroundings of the moving object 100 in order to acquire information needed for autonomous traveling of the e-pallet (moving object 100). The sensor 101 includes, for example, a stereo camera, a laser scanner, a LIDAR, a radar, or the like. Information acquired by the sensor 101 is transmitted to the controller 103, and is used by the controller 103 for recognition or the like of an obstacle or a traveling lane surrounding the e-pallet (moving object 100). The positional information acquisition unit 102 acquires a current position of the e-pallet (moving object 100). For example, the positional information acquisition unit 102 includes a GPS receiver or the like. Information acquired by the positional information acquisition unit 102 is also transmitted to the controller 103, and is used, for example, in calculating a route to the position of the user as a destination using the current position of the e-pallet (moving object 100).

The operation plan generation unit 1031 acquires an instruction from the management server 400 through the communication unit 105 and generates an operation plan of the host vehicle. The instruction includes information relating to a departure place and a destination given to the e-pallet (moving object 100). Accordingly, the operation plan generation unit 1031 calculates a movement route based on the positional information of the user given from the management server 400 and the position of the host vehicle obtained by the positional information acquisition unit 102 and generates an operation plan for movement along the movement route. The operation plan includes data relating to the calculated route, along which the e-pallet (moving object 100) travels, and data defining processing to be executed by the e-pallet (moving object 100) in a part or the whole of the route.

The environment detection unit 1032 detects an environment surrounding the e-pallet (moving object 100) needed for autonomous traveling based on data acquired by the sensor 101. A target of detection is, but not limited to, for example, the number or positions of other moving objects surrounding the host vehicle, the number or positions of obstacles (for example, pedestrians, bicycles, structures, buildings, or the like) surrounding the host vehicle, the structure of roads, road signs, or the like. Any target of detection may be applied as long as the target of detection is needed for autonomous traveling. Data (hereinafter, referred to as environment data) relating to the surrounding environment of the e-pallet (moving object 100) detected by the environment detection unit 1032 is transmitted to the traveling controller 1033.

The traveling controller 1033 generates a control command for controlling autonomous traveling of the e-pallet (moving object 100) based on the operation plan generated by the operation plan generation unit 1031, the environment data generated by the environment detection unit 1032, and the positional information acquired by the positional information acquisition unit 102. For example, the traveling controller 1033 generates the control command in order to make the moving object 100 travel along a predetermined route such that an obstacle does not enter a predetermined safety area centering on the moving object 100.

The drive unit 104 is a unit that makes the e-pallet (moving object 100) travel based on the control command generated by the traveling controller 1033. The drive unit 104 includes, for example, a motor that drives the wheels TR-1 to TR-4, an inverter, a brake, a steering mechanism, and the like, and the motor, the brake, or the like is driven according to the control command, whereby autonomous traveling of the moving object 100 is implemented. The communication unit 105 connects the e-pallet (moving object 100) to the network N1.

A procedure of deciding an order of vehicle allocation for the e-pallet (moving object 100), and the like are the same as those in the embodiment described above. According to the above-described embodiment, even in a large facility on an extensive site, or the like, it is possible to quickly cope with the demand of the user without unnecessarily increasing the number of toilets, AEDs, or fire extinguisher.

Fifth Embodiment

FIG. 17 is a schematic view showing a vehicle allocation service system according to a fifth embodiment of the disclosure. The biological information is, in principle, a physical quantity digitalized by a sensor. Note that, in the fifth embodiment, the user inputs information indicating that the user has a micturition desire or a defecation desire to the user terminal 200, and information input from the user is processed as the biological information. The positional information of the user is obtained based on GPS information from a GPS receiver or the like in the user terminal 200 belonging to or carried with the user. In FIG. 17, the user terminal 200 is a smartphone, and an application screen 201 (hereinafter, referred to as an app screen 201) installed on the smartphone is illustrated.

The app screen 201 allows various inputs with a touch key system on a touch panel, and in a case where the user has a micturition desire or a defecation desire, the user presses a toilet key 212 on the app screen 201. In a lower portion of the app screen 201, an emergency key 213 indicating the degree of emergency is arranged. Similarly to the example shown in FIG. 3, a numerical value 1 of the emergency key 213 designates normal arrival within 30 minutes, 2 designates priority (arrival within 15 minutes), and 3 designates the highest priority (arrival within three minutes). Accordingly, the user can perform a selection input of the degree of emergency on the app screen 201. Then, the user terminal 200 transmits the input information to the management server 400 through the network N1. A procedure for deciding an order of vehicle allocation for the moving object 100, and the like are the same as those in the first embodiment described above. Similarly to the micturition desire, the user may input an AED key 211 in a case where the AED is needed, and may input an ambulance key 210 in a case where emergency transport with an ambulance is needed.

In regard to the micturition desire or the defecation desire, other kinds of information may be input. For example, the user inputs a start time of dining-together (a gathering for drinking) at a restaurant or the like as other kinds of information. In the user terminal 200, a time when the user normally feels a micturition desire after the start time is estimated. The time can be determined by analyzing anthropometric surveys of micturition and defecation patterns of a large number of users or the user of the user terminal 200 and trends. In the estimation, as in the first embodiment or the like, it is desirable that the user terminal 200 extracts features based on detection values of the pressure sensor or the optical sensor measuring pulse or blood pressure as the biological information, variation patterns, or the like, and executes processing in combination with a lapse of time.

In a large facility on an extensive site, or the like, as in the fifth embodiment, a plurality of moving objects 100 may be provided as e-pallets. According to the above-described embodiment, in regard to direct demand of a user, the e-pallet (moving object 100) is selected in addition to the degree of emergency, and the order of vehicle allocation is decided according to the degree of emergency. Therefore, it is possible to execute countermeasures or actions to demands from a plurality of users in emergency correctly such that the satisfaction of the users is obtained.

Sixth Embodiment

FIG. 18 is a schematic view showing a vehicle allocation service system according to a sixth embodiment of the disclosure. A difference from other embodiments is that, in the vehicle allocation service system of the sixth embodiment, a hospital 601 and other medical institutions 602 are connected to the network N1, and information sharing with management server 400 is achieved. Other medical institutions 602 include a large-scale medical facility, such as the National Research Center for Advanced and Specialized Medical Car, the National Institute of Infectious Diseases, or a large hospital, a long-term care health facility, a pharmacy that prepares a medicine, and facilities that provides other medical care.

The management server 400 refers to the state database 410 (FIGS. 3 to 5, and 6) in a case where determination on the state information of the user is performed based on the acquired biological information, and transmits the biological information of the user to the hospital 601 and other medical institutions 602. Then, the management server 400 acquires, from the hospital 601 and other medical institutions 602, information and diagnosis utilizing the expertise of the hospital 601 and other medical institutions 602. With this, it is possible to select an appropriate moving object 100 in a more advanced manner in addition to the condition based on the state database 410 (FIGS. 3 to 5, and 6). A procedure for deciding an order of vehicle allocation for the moving object 100, and the like are the same as those in the first embodiment described above.

Alternatively, in emergency, such as a case where the user is ill or injured, the moving object 100 may not only simply move to the position of the user, and thereafter, may but also carry the user to the hospital 601 for medical treatment. In this case, it is possible to quickly and more appropriately enable initial response, inspection, follow-up observation, and treatment to the user through the network N1 during carrying or preparation in the hospital 601.

OTHER EMBODIMENTS

The above-described embodiments are just examples, and the disclosure may be appropriately modified to be executed without departing from the spirit and scope of the disclosure. The processing or units described in the present disclosure can be freely combined and implemented as long as no technical contradiction arises. In particular, the vehicle allocation service systems according to the first embodiment to the sixth embodiment may be selected respectively and combined optionally.

Processing described to be executed by one apparatus may be shared and executed by a plurality of apparatuses. Alternatively, processing described to be executed by different apparatuses may be executed by one apparatus. In a computer system, a hardware configuration (server configuration) that implements each function may be flexibly changed.

The disclosure may also be implemented by supplying a computer program mounted with the functions described in the above-described embodiments to a computer and causing one or more processors in the computer to read and execute the program. Such a computer program may be provided to the computer by a non-transitory computer-readable storage medium connectable to a system bus of the computer or may be provided to the computer through a network. The non-transitory computer-readable storage medium includes, for example, any type of disk, such as a magnetic disk (a Floppy (Registered Trademark) disk, a hard disk drive (HDD), or the like), or an optical disk (a CD-ROM, a DVD, a Blu-ray disc, or the like), a read only memory (ROM), a random access memory (RAM), an EPROM, an EEPROM, a magnetic card, a flash memory, an optical card, or any type of medium suitable for storing electronic instructions.

What is claimed is:

1. A vehicle allocation service system comprising:
   circuitry configured to acquire biological information and positional information of a user;
   circuitry configured to determine whether the acquired biological information satisfies a specific condition that is stored in advance;
   circuitry configured to select a moving object to be provided to the user according to whether the acquired biological information satisfies the specific condition that is stored in advance;
   circuitry configured to acquire priority added to the satisfied condition of the biological information of the user and decide an order of vehicle allocation for the selected moving object according to the priority; and
   circuitry configured to instruct the selected moving object to move according to the positional information.

2. The vehicle allocation service system according to claim 1, further comprising a state database configured to store the biological information and a kind of the moving object to be provided to the user in association with each other,
   wherein the circuitry configured to select a moving object to be provided to the user according to whether the acquired biological information satisfies the specific condition that is stored in advance is further configured to select the moving object to be provided to the user based on the state database.

3. The vehicle allocation service system according to claim 2, wherein:
   the circuitry configured to acquire biological information and positional information of a user is provided in a user terminal that is able to perform communication with a management apparatus configured to manage the moving object; and
   the state database and the circuitry configured to select a moving object to be provided to the user according to whether the acquired biological information satisfies the specific condition that is stored in advance are provided in the management apparatus.

4. The vehicle allocation service system according to claim 3, wherein:
   the circuitry configured to acquire biological information and positional information of a user, the state database, and the circuitry configured to select a moving object to be provided to the user according to whether the acquired biological information satisfies the specific condition that is stored in advance are provided in the user terminal that is able to perform communication with the management apparatus; and
   information regarding the moving object selected by the user terminal is transmitted to the management apparatus.

5. The vehicle allocation service system according to claim 3, wherein:
   the user terminal further includes an acceleration sensor configured to acquire acceleration information; and
   the circuitry configured to select a moving object to be provided to the user according to whether the acquired biological information satisfies the specific condition that is stored in advance is further configured to select the moving object to be provided to the user based on the biological information and the acceleration information.

6. The vehicle allocation service system according to claim 3, wherein the moving object comprises:
   circuitry configured to acquire an instruction from the management apparatus; and
   a movement controller configured to perform control such that the moving object moves to a position indicated by the positional information based on the instruction.

7. The vehicle allocation service system according to claim 1, wherein the circuitry configured to select a moving object to be provided to the user according to whether the acquired biological information satisfies the specific condition that is stored in advance is further configured to select a moving object having a toilet function in a case where determination is made that the user has a micturition desire or a defecation desire based on the biological information.

8. The vehicle allocation service system according to claim 1, wherein the circuitry configured to select a moving object to be provided to the user according to whether the acquired biological information satisfies the specific condition that is stored in advance is further configured to select a moving object having a function as an ambulance in a case where determination is made that emergency transport of the user is needed based on the biological information.

9. The vehicle allocation service system according to claim 1, further comprising circuitry configured to obtain health data or an activity amount of the user based on the acquired biological information,
  wherein the circuitry configured to select a moving object to be provided to the user according to whether the acquired biological information satisfies the specific condition that is stored in advance is further configured to select the moving object based on the health data or the activity amount.

10. The vehicle allocation service system according to claim 1, wherein the biological information is any one of bladder expansion rate, heart rate, and body temperature.

11. The vehicle allocation service system according to claim 1, wherein the biological information is bladder expansion rate, and the specific condition is a degree of expansion of the bladder.

12. A vehicle allocation service method comprising:
  with a management apparatus configured to manage a moving object,
  acquiring biological information and positional information of a user;
  selecting a moving object to be provided to the user based on whether the acquired biological information satisfies a specific condition that is stored in advance;
  acquiring priority added to a satisfied condition of the biological information;
  deciding an order of vehicle allocation for the selected moving object according to the priority; and
  giving an instruction for movement according to the positional information.

13. A non-transitory computer-readable storage medium storing thereon a program, executed by a processor that causes a computer to implement
  a function of acquiring biological information and positional information of a user;
  a function of selecting a moving object to be provided to the user based on whether the acquired biological information satisfies a specific condition that is stored in advance;
  a function of acquiring priority added to a satisfied condition of the biological information;
  a function of deciding an order of vehicle allocation for the selected moving object according to the priority; and
  a function of giving an instruction for movement according to the positional information.

14. The non-transitory computer-readable storage medium according to claim 13, wherein:
  a state database configured to store the biological information and a kind of the moving object to be provided to the user in association with each other is provided; and
  the selection function selects the moving object based on the state database.

* * * * *